(12) United States Patent
Chen et al.

(10) Patent No.: US 11,673,116 B2
(45) Date of Patent: Jun. 13, 2023

(54) METHOD FOR PRODUCING SUPERABSORBENT POLYMER

(71) Applicant: FORMOSA PLASTICS CORPORATION, Kaohsiung (TW)

(72) Inventors: Zhong-Yi Chen, Kaohsiung (TW); Cheng-Lin Lee, Kaohsiung (TW); Feng-Yi Chen, Kaohsiung (TW); Yu-Yen Chuang, Kaohsiung (TW)

(73) Assignee: FORMOSA PLASTICS CORPORATION, Kaohsiung (TW)

( * ) Notice: Subject to any disclaimer, the term of this patent is extended or adjusted under 35 U.S.C. 154(b) by 79 days.

(21) Appl. No.: 17/398,578

(22) Filed: Aug. 10, 2021

(65) Prior Publication Data
US 2022/0040671 A1 Feb. 10, 2022

(30) Foreign Application Priority Data
Aug. 10, 2020 (TW) ................. 109127132

(51) Int. Cl.
*B01J 20/26* (2006.01)
*B01J 20/24* (2006.01)
*B01J 20/28* (2006.01)
*B01J 20/30* (2006.01)
*B01J 20/32* (2006.01)

(52) U.S. Cl.
CPC ............ *B01J 20/267* (2013.01); *B01J 20/24* (2013.01); *B01J 20/28035* (2013.01); *B01J 20/3021* (2013.01); *B01J 20/3071* (2013.01); *B01J 20/3282* (2013.01); *B01J 2220/68* (2013.01)

(58) Field of Classification Search
CPC ......... B01J 20/26; B01J 20/267; B01J 20/24; B01J 20/28035; B01J 20/3021; B01J 20/3071; B01J 20/3282; B01J 2220/68
USPC ...................................... 502/402
See application file for complete search history.

(56) References Cited

U.S. PATENT DOCUMENTS

| | | | |
|---|---|---|---|
| 5,980,879 A | 11/1999 | Hiroki et al. | |
| 6,346,569 B1 | 2/2002 | Irizato et al. | |
| 6,663,949 B1 | 12/2003 | Tanaka et al. | |
| 6,849,665 B2 | 2/2005 | Frenz et al. | |
| 7,868,075 B2 | 1/2011 | Taniguchi et al. | |
| 8,658,146 B2 | 2/2014 | Furno et al. | |
| 9,913,467 B2 | 3/2018 | Wooley | |
| 10,071,003 B2 | 9/2018 | Roe et al. | |
| 10,550,243 B2 | 2/2020 | Chen et al. | |
| 2001/0053807 A1 | 12/2001 | Miyake et al. | |
| 2003/0004479 A1 | 1/2003 | Ueda et al. | |
| 2004/0048955 A1 | 3/2004 | Wada et al. | |
| 2004/0106745 A1 | 6/2004 | Nakashima et al. | |
| 2015/0290052 A1 | 10/2015 | Forsgren Brusk et al. | |
| 2015/0306272 A1 | 10/2015 | Karim et al. | |
| 2018/0282515 A1 | 10/2018 | Chen et al. | |

FOREIGN PATENT DOCUMENTS

| | | |
|---|---|---|
| CN | 1863519 B | 10/2012 |
| CN | 103340722 B | 7/2015 |
| CN | 108371724 A | 8/2018 |
| CN | 108659248 A | 10/2018 |
| CN | 110075342 A | 8/2019 |
| EP | 1275404 A1 | 1/2003 |
| EP | 1404385 B1 | 1/2007 |
| JP | 56-131608 A | 10/1981 |
| JP | 57-44627 A | 3/1982 |
| JP | 58-42602 A | 3/1983 |
| JP | S58117222 A | 7/1983 |
| JP | S60163956 A | 8/1985 |
| JP | H1113406 A | 5/1989 |
| JP | H1255814 A | 10/1989 |
| JP | H1292004 A | 11/1989 |
| JP | H2153903 A | 6/1990 |
| JP | 07-165981 A | 6/1995 |
| JP | 11-116829 A | 4/1999 |
| TW | 200301268 A | 7/2003 |
| WO | WO03028778 A2 | 4/2003 |
| WO | WO2009048145 A1 | 4/2009 |

*Primary Examiner* — Edward M Johnson
(74) *Attorney, Agent, or Firm* — Muncy, Geissler, Olds & Lowe, P.C.

(57) ABSTRACT

The present invention relates to a superabsorbent polymer and a method for producing the same. The superabsorbent polymer includes a core layer polymerized with monomers having carboxylic group, a first shell layer formed from a surface crosslinking agent, and a second shell layer formed from zingiberaceae extracts. By a surface modification on the first shell layer performed from a specific amount of the zingiberaceae extracts, the superabsorbent polymer produced according to the method for producing the same has a good antimicrobial property and deodorizing effects, and retains an original absorbent property.

4 Claims, 2 Drawing Sheets

METHOD FOR PRODUCING SUPERABSORBENT POLYMER

RELATED APPLICATION

This application claims priority to an earlier Taiwan Application Ser. No. 109127132, filed on Aug. 10, 2020 which is incorporated herein by reference in its entirety.

BACKGROUND

Field of Invention

The present invention relates to a superabsorbent polymer and a method for producing the same, and more particularly relates to a superabsorbent polymer having a good antimicrobial property and deodorizing effects and a method for producing the same.

Description of Related Art

Absorbent resin is widely used as water-retaining agents in agricultural or horticultural aspects, anti-dew condensation agents in building materials, and materials for removing moisture from petroleum, water-proof coating agents on an outer layer of cables and hygiene supplies. For example, diapers, women's hygiene products and disposable wipes etc., and especially mostly used in the diapers.

The current developing orientation is functional diapers, in particular adult diapers. In addition to emphasizing the absorption capacity and dryness, diapers with antimicrobial and deodorizing abilities are further directed to. Based on a demand for antimicrobial and deodorizing abilities, a variety of researches are carried out to develop the absorbent resin having antimicrobial and deodorizing abilities.

In the technical field of the present invention, conventional methods for providing antimicrobial or deodorizing ability is to disperse zeolite particles in the absorbent resin to equip the absorbent resin with a deodorizing ability. As disclosed in U.S. Pat. No. 5,980,879, the addition of zeolite particles in a polymeric reaction to provide the absorbent resin with a deodorizing ability. However, the absorption capacity of the absorbent resin is greatly reduced because the addition amount of the zeolite must be at least 25%. Besides, U.S. Patent Publication No. 20150290052 adds activated carbon or zeolite particles to the diaper absorbent. Although the diaper absorbent has the deodorizing ability, the aforementioned particles easily leak from the production equipment, and even suspend in ambient air of the plant, further causing damages to health of the on-site operators.

WO 2009/048145 discloses a method for preparing absorbent resin by adding bamboo extracts or tea extracts onto the surface of absorbent resin or into a polymeric reaction. However, since the extracts affect the polymeric reaction, it reduces the water absorption capacity of the absorbent resin, and increases residual monomers in the absorbent resin to cause skin swollen. Besides, U.S. Patent Publication No. 20030004479 and U.S. Patent Publication No. 20040048955 disclose that the powder obtained from pulverized bamboo or tea is added to the surface of the absorbent resin. Since the dispersibility of the powder of the pulverized bamboo or tea is poor and difficult to be uniformly mixed with the absorbent resin, the antimicrobial and deodorizing abilities are bad.

In addition, U.S. Pat. No. 6,663,949, European Patent No. EP 1404385, and U.S. Pat. No. 7,868,075 disclose that the use of activated carbon, nano-silver ions or zeolite with surfaces coated with silver ions reduces odors or inhibit bacterial growth. European Patent Publication No. EP 1275404 discloses that the use of cyclodextrin or its derivatives to be mixed with the absorbent resin to reduce the occurrence of odors. Besides, U.S. Patent Publication No. 20150306272 also discloses that the thermal treatment of 1,2-decanediol and absorbent resin to reduce the occurrence of odor. However, these patents cannot provide absorbent resin with antimicrobial and deodorizing abilities, but only have a better ability to inhibit ammonia.

Besides, WO 2003/028778 discloses a method for producing an absorbent resin. The method lowers the pH of the absorbent resin to produce an antimicrobial absorbent resin. U.S. Patent Publication No. 20010053807 discloses that the addition of aminoacetic acid also can reduce the occurrence of odor. However, the absorbent resin produced by the above method has bad urine tolerance under pressure.

In addition, Japan Patent Publication No. 1995-165981 discloses a mixture of an absorbent resin and a phosphate compound. Japan Patent Publication No. 1999-116829 discloses that a mixture of an absorbent resin and a silicate compound. Although the antimicrobial ability of the absorbent resin can be improved by mixing the aforementioned compounds, the absorption rate against pressure is decreased.

U.S. Pat. No. 8,658,146 discloses that the gallotannin and its derivative are mixed with an absorbent resin. Although an absorbent resin having a deodorizing ability can be produced, its cost is high and it is not suitable for long-term preservation due to problems of yellowing or browning under high temperature and high humidity.

Besides, U.S. Pat. No. 10,550,243 discloses that adding solution of natural sapindaceae to the absorbent resin to perform a surface modification. Although it provides the absorbent resin with antimicrobial and deodorizing abilities, an antimicrobial ability of gram-positive bacteria (such as *Staphylococcus aureus*) is bad.

In view of these, it is necessary to develop an absorbent resin having a good antimicrobial property and deodorizing effects and a method for producing the same to solve the aforementioned drawbacks of the well-known absorbent resin.

SUMMARY

In view of the above problems, an aspect of the present invention is to provide a superabsorbent polymer. The superabsorbent polymer comprises a core layer polymerized with monomers having carboxylic group, a first shell layer formed from a surface crosslinking agent and a second shell layer formed from zingiberaceae extracts. By a surface modification on the first shell layer performed from a specific amount of the zingiberaceae extracts, the superabsorbent polymer produced according to the method for producing the same has a good antimicrobial property and deodorizing effects, and retains an original absorbent property.

Another aspect of the present invention is to provide a method for producing the superabsorbent polymer. The method for producing the superabsorbent polymer is used to produce the aforementioned superabsorbent polymer, wherein by a surface modification performed from a specific amount of the zingiberaceae extracts; the resulted superabsorbent polymer has a good antimicrobial property and deodorizing effects, and retains an original absorbent property.

According to an aspect of the present invention, superabsorbent polymer is provided. The superabsorbent polymer comprises a core layer polymerized with monomers having carboxylic group, the first shell layer formed from a surface crosslinking agent and the second shell layer formed from zingiberaceae extracts, wherein the first shell layer encapsulates an outer surface of the core layer and the second shell layer encapsulates an outer surface of the first shell layer. Based on a total weight of the core layer and the first shell layer as 100 weight parts, an amount of the zingiberaceae extracts is 0.005 weight parts to 0.2 weight parts.

According to another embodiment of the present invention, the zingiberaceae extracts comprise underground rhizome extracts, stem extracts, flower extracts and/or leaf extracts of zingiberaceae plants.

According to another aspect of the present invention, the zingiberaceae extracts are made by an extraction method. In the extraction method, a pulverizing treatment is performed to zingiberaceae plants for obtaining pulverized material of the zingiberaceae plants. Next, an extraction treatment with hot water is performed to the pulverized material of the zingiberaceae plants for obtaining crude extracts. Then, a vacuum distillation treatment is performed to the crude extracts for obtaining the zingiberaceae extracts.

According to an embodiment of the present invention, the zingiberaceae plants comprise *Curcuma longa*, alpinia zerumbet, *hedychium coronarium, zingiber zerumbet*, alpinia speciose cv variegata, peacock ginger, *Curcuma alismatifolia* and/or *Curcuma roscoeana*.

According to another aspect of the present invention, a method for producing superabsorbent polymer is provided. In the method for producing superabsorbent polymer, a free radical polymerization reaction is performed to monomers having carboxylic group for forming a core layer. Next, a surface crosslinking reaction is performed to the core layer by using a surface crosslinking agent for forming a first shell layer, wherein the first shell layer encapsulates an outer surface of the core layer. Then, a surface modification reaction is performed to the first shell layer by using zingiberaceae extracts for forming a second shell layer, wherein the second shell layer encapsulates an outer surface of the first shell layer. Based on a total weight of the core layer and the first shell layer as 100 weight parts, an amount of the zingiberaceae extracts is 0.005 weight parts to 0.2 weight parts.

According to another embodiment of present invention, the zingiberaceae extracts comprise underground rhizome extracts, stem extracts, flower extracts and/or leaf extracts of zingiberaceae plants.

According to another embodiment of present invention, the zingiberaceae extracts are made by an extraction method. In the extraction method, a pulverizing treatment is performed to zingiberaceae plants for obtaining pulverized material of the zingiberaceae plants. Next, an extraction treatment with hot water is performed to the pulverized material of the zingiberaceae plants for obtaining crude extracts. Then, a vacuum distillation treatment is performed to the crude extracts for obtaining the zingiberaceae extracts.

According to another embodiment of present invention, the zingiberaceae plants comprise *Curcuma longa*, alpinia zerumbet, *hedychium coronarium, zingiber zerumbet*, alpinia speciose cv variegata, peacock ginger, *Curcuma alismatifolia* and/or *Curcuma roscoeana*.

In an application of the superabsorbent polymer and the method for producing the same of the present invention, in where the superabsorbent polymer comprises a core layer polymerized with monomers having carboxylic group, a first shell layer formed from a surface crosslinking agent, and a second shell layer formed from zingiberaceae extracts. By a surface modification on the first shell layer performed from a specific amount of the zingiberaceae extracts, the resulted superabsorbent polymer has a good antimicrobial property and deodorizing effects, and retains an original absorbent property.

BRIEF DESCRIPTION OF THE DRAWINGS

Now please refer to description below and accompany with corresponding drawings to more fully understand embodiemnts of the present invention and advantages thereof. It was emphasized that all kinds of characteristics are not drawn in scale and olny for illustrative purpose. The description regarding to the drawings as follows.

DETAILED DESCRIPTION

A manufacturing and usage of embodiments of the present invention are discussed in detail below. However, it could be understood that embodiments provide much applicable invention conception which can be implemented in various kinds specific contents. The specific embodiments discussed are only for illustration, but not be a limitation of scope of the present invention.

Figure 1:
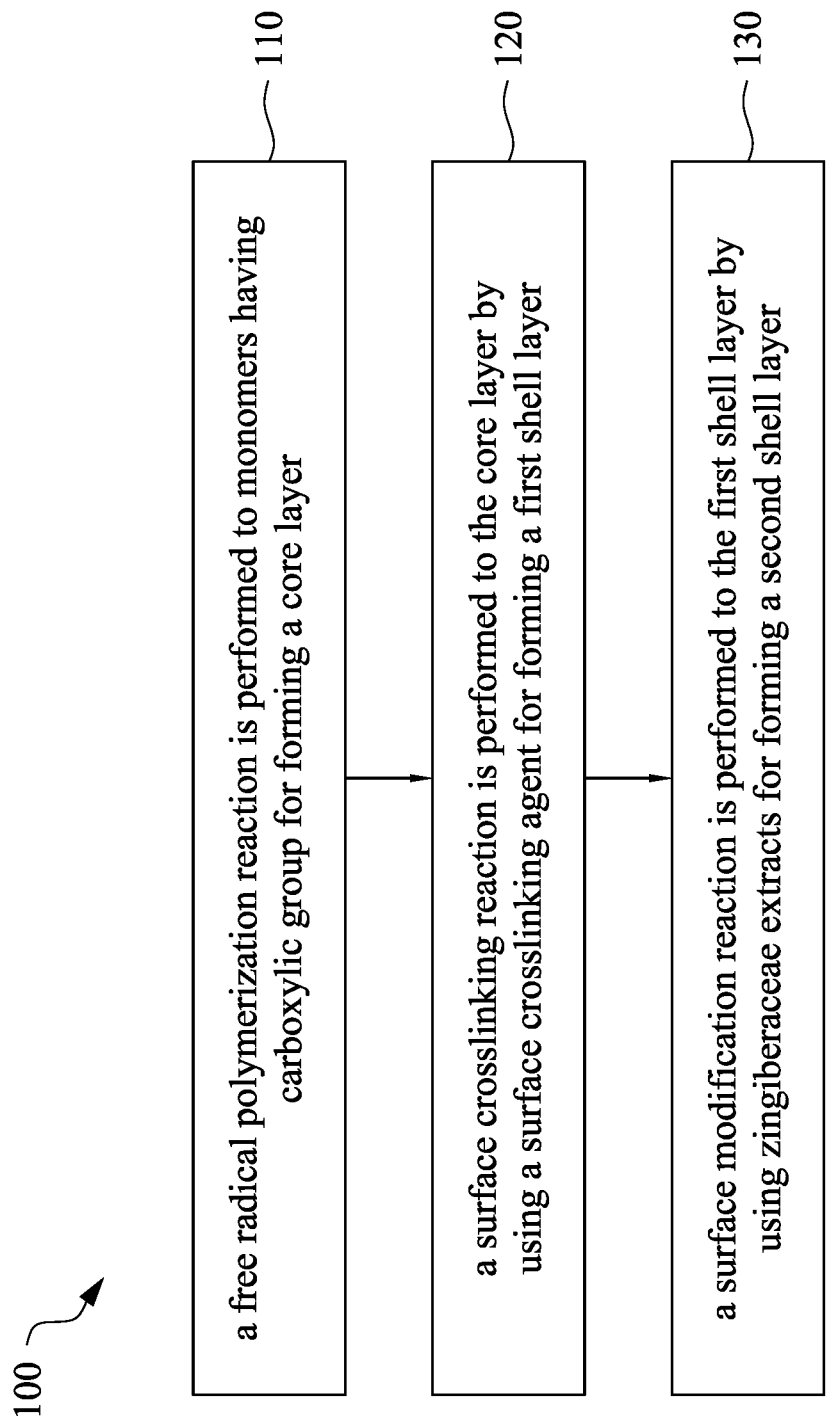
FIG. 1 illustrates a flow chart of a method for producing superabsorbent polymer according to an embodiment of the present invention.

Referring to FIG. 1, it illustrates a flow chart of a method for producing superabsorbent polymer according to an embodiment of the present invention. In the method 100 for producing the superabsorbent polymer, a free radical polymerization reaction is first performed to monomers having carboxylic group for forming a core layer, as shown in an operation 110.

Monomers having carboxylic group are aqueous unsaturated monomer. In some embodiments, monomers having carboxylic group can comprise, but are not limited to, acrylic compounds, other suitable compounds having carboxylic group and unsaturated double bond or any combination of the aforementioned compounds. In some specific examples, the acrylic compounds can comprise, but are not limited to, acrylic acid, methacrylic acid, 2-propenylamine-2-methylpropane sulfonic acid or any combination of the aforementioned compounds. In other specific examples, the other suitable compounds having carboxylic group and unsaturated double bond can comprise, but are not limited to, maleic acid, maleic acid anhydride, fumaric acid, fumaric acid anhydride and etc. The monomers having carboxylic group can be used alone or in combination.

In another some embodiments, the monomers having carboxylic group can selectively comprise other hydrophilic monomers with unsaturated double bonds. In other specific examples, the other hydrophilic monomers with unsaturated double bonds can comprise, but are not limited to, acrylamide, methacrylamide, 2-carboxyethyl acrylate, 2-carboxyethyl methacrylate, methyl acrylate, acrylic acid ethyl ester, dimethylaminopropyl acrylamide, propyl acrylamide trimethylammonium chloride and etc. Further, it is understood that an amount of the aforementioned unsaturated monomers having carboxylic group is based on the principle of not destroying the physical properties of the superabsorbent polymer.

During the operation 110, the monomers having carboxylic group are dissolved in water for forming an aqueous solution containing the monomers having carboxylic group. A pH value of the aqueous solution containing the monomers having carboxylic group can be adjusted by neutralizing a part of carboxylic group of the monomers having carboxylic group to control a pH value of products of superabsorbent polymer. In some embodiments, the pH value of the aqueous solution containing the monomers having carboxylic group is not less than 5.5, and preferably is 5.6 to 6.5. When the pH value of the aqueous solution containing the monomers having carboxylic group is not less than 5.5, after polymerization, an appropriate amount of the monomers is left in a gel, thereby providing the superabsorbent polymer with good physical properties.

A neutralizer can be used to neutralize the aforementioned monomers having carboxylic group. In some embodiments, the neutralizer can comprise, but is not limited to, hydroxides of alkali metal element or alkaline earth element, a carbonate compound, or any combination thereof, and/or other suitable basic compounds. In some specific examples, the neutralizer can comprise, but is not limited to, sodium hydroxide, potassium hydroxide, sodium carbonate, potassium carbonate, sodium bicarbonate, potassium bicarbonate, ammonia compounds or any combination thereof. Besides, the neutralizers can be used alone or in combination.

After the monomers having carboxylic group are neutralized with the neutralizer, carboxylic groups of the monomers having carboxylic group can form sodium salt, potassium salt or ammonium salt and etc. In some embodiments, a neutralization ratio of the aqueous solution containing the monomers having carboxylic group can be 45 mole % to 85 mole % and preferably is 50 mole % to 75 mole %. When the neutralization ratio of the aqueous solution containing the monomers having carboxylic group is 45 mole % to 85 mole %, the pH value of the product produced by the superabsorbent polymer is slightly acidic (i.e. the pH value of 5.6 to 6.5) to neutral (i.e. the pH value of 7) in which the product is safe to be suitable to contact with the human body.

In some embodiments, the amount of the monomers having carboxylic group of the present invention is not particularly limited. In other embodiments, based on the amount of the aqueous solution containing the monomers having carboxylic group as 100 weight parts, the amount of the monomers having carboxylic group is 20 weight parts to 55 weight parts and preferably is 30 weight parts to 45 weight parts. When the amount of the monomers having carboxylic group is 20 weight parts to 55 weight parts, the gel after polymerization is not too softy to decrease viscosity, thereby facilitating mechanical processing. A concentration of the aqueous solution containing the monomers having carboxylic group is not close to the saturated concentration and is easy to be prepared. The polymerization reaction proceeds gently, such that the reaction heat is easy to control.

In some embodiments, the aqueous solution containing the monomers having carboxylic group can selectively comprise aqueous polymers to decrease cost. In such embodiments, the aqueous polymers can comprise, but are not limited to, partially saponified or fully saponified polyvinyl alcohol, polyethylene glycol, polyacrylic acid, polypropylene amide, starch and/or starch derivatives. In some specific examples, the starch and the starch derivatives can comprise, but are not limited to, methyl cellulose, acrylate methyl cellulose, ethyl cellulose and etc.

Molecular weight of the aforementioned aqueous polymers is not particularly limited. Ppreferably, the aqueous polymers can be starch, partially saponified polyvinyl alcohol, fully saponified polyvinyl alcohol and any combination thereof. Based on the amount of the aqueous solution containing the monomers having carboxylic group as 100 weight parts, an amount of the aqueous polymers can be 0 to 20 weight parts, preferably is 0 to 10 weight parts, and more preferably is 0 to 5 weight parts.

During the operation 110, the monomers having carboxylic group are subjected to a free radical polymerization reaction by adding internal crosslinking agents and polymerization initiators for forming a crosslinking structure, and the crosslinking structure is a core layer. The free radical polymerization reaction provides the gel of the superabsorbent polymer with appropriate processability. The internal crosslinking agents can comprise, but are not limited to, compounds having at least two unsaturated double bond groups, compounds having at least two epoxy groups or any combination of the aforementioned compounds.

In some specific examples, the compounds having at least two unsaturated double bond groups can comprise, but are not limited to, N,N'-bis(2-propenyl)amine, N,N'-methylene bisacrylamide, N,N'-methylene bismethacrylamide, propylene acrylate, ethylene glycol diacrylate, poly(ethylene glycol) diacrylate, ethylene glycol dimethacrylate, polyethylene glycol dimethyl acrylate, glycerol triacrylate, glycerol trimethacrylate, glycerol added ethylene oxide triacrylate or trimethacrylate, trimethylolpropane added ethylene oxide triacrylate ester or trimethacrylate, trimethylolpropane trimethacrylate, trimethylolpropane triacrylate, N,N,N-tris(2-propenyl)amine, diacrylic acid ethylene glycol ester, polyoxyethylene triacrylate glycerol ester, diethylene polyoxyethylene glycerol triacrylate, dipropylene triethylene glycol ester or any combination thereof.

In some specific examples, the compounds having at least two epoxy groups can comprise, but are not limited to, sorbitol polyglycidyl ether, polyglycerol polyglycidyl ether, ethylene glycol diglycidyl ether, diethylene glycol diglycidyl ether, polyethylene glycol diglycidyl ether, diglycerol polyglycidyl ether or any combination thereof. Besides, the internal crosslinking agents can be used alone or in combination.

In some embodiments, based on a total amount of the neutralized monomers having carboxylic group, the internal crosslinking agents and the polymerization initiators as 100 weight parts, an amount of the internal crosslinking agents is 0.001 weight parts to 5 weight parts, and preferably is 0.01 weight parts to 3 weight parts. When the amount of the internal crosslinking agents is 0.001 weight parts to 5 weight parts, the gel after polymerization decreases viscosity for facilitating mechanical processing and has good absorbent property for enhancing performance of the superabsorbent polymer.

During the operation 110, the polymerization initiators are used to produce free radical for inducing the polymerization reaction. The polymerization initiators comprise, but are not limited to, thermally decomposing initiators, redox initiators and any combination thereof. When the redox initiators and the thermally decomposing initiators are used in combination, the redox initiators first undergo a reaction to generate free radicals. The free radicals transfer to monomers having carboxylic group to initiate a first stage of the free radical polymerization reaction. The first stage of the free radical polymerization reaction releases a lot of heat, and a high temperature caused by the heat reaches decomposition temperature of the thermally decomposing initiators. The high temperature initiates decomposition of the thermally decomposing initiators to induce a second stage of the free radical polymerization reaction, thereby enhancing completeness of the free radical polymerization reaction.

In some embodiments, the thermally decomposing initiators can comprise, but are not limited to, peroxides and/or azo compounds. In some specific examples, the peroxides can comprise, but are not limited to, hydrogen peroxide, di-t-butyl peroxide, a peroxyamide or a persulfate (ammonium salt or alkali metal salt) and etc. In another specific examples, the azo compound can comprise, but are not limited to, 2,2'-azobis (2-amidinopropane) dihydrochloride salt or 2,2'-azobis (N,N-dimethylene isobutylamidine) dihydrochloride salt and etc. In another embodiment, the redox initiators can comprise, but are not limited to, acidic sulfite salt, thiosulfate salt, ascorbic acid or ferrous salt and etc.

In some embodiments, based on a weight of acrylate salt (i.e. an amount of the neutralized monomers having carboxylic group) as 100 weight percentages, an amount of the polymerization initiators can be 0.001 weight percentages to 10 weight percentages and preferably is 0.1 weight percentages to 5 weight percentages. When the amount of the polymerization initiators is 0.001 weight percentages to 10 weight percentages, a reaction rate of the free radical polymerization reaction is moderate to meet economical effect and easy to control the heat of reaction, so that the degree of polymerization is appropriate.

The aforementioned free radical polymerization reaction can be subjected in a conventional batch reaction vessel or on a conveyor belt reactor. In some embodiments, the gel made by the free radical polymerization reaction is cut into gel particles having a diameter of 20 mm or less using a crusher, and the diameter is preferably not more than 10 mm in diameter. Then, screening step is performed.

The aforementioned screening step is to screen out gel particles having a diameter of 2.00 mm or less, and the diameter of gel particles is preferably 0.05 mm to 1.50 mm. If the diameter of the gel particles is more than 2.00 mm, the gel particles are sent back to the reactor for re-chopping. When the diameter of the gel particles is less than 0.05 mm, after drying and pulverizing treatments, it is easy to increase an amount of fine powder of the product of superabsorbent polymer. When the diameter of the gel particles is more than 2.00 mm, poor heat conduction easily results in the product of the superabsorbent polymer with high residual monomers and poor physical properties when the gel particles are dried. According to one embodiment of the present invention, when a particle size distribution of the gel particles is narrower, the physical properties of the dried gel particles are better, which is facilitated to control drying time and drying temperature.

In some embodiments, after the gel particles are screened, they are dried, in which the drying temperature can be 100° C. to 180° C. When the drying temperature is less than 100° C., it leads to more drying time and to decreasing economic benefits. When the drying temperature is more than 180° C., the internal crosslinking agents prematurely undergo the crosslinking reaction and the residual monomers are unable to be removed efficiently in the subsequent drying process due to an overly high crosslinking degree, such that the residual monomers are unable to be reduced.

In some embodiments, after dried, the gel particles are pulverized and screened by a given particle size. The given particle size for screening is 0.06 mm to 1.00 mm, preferably is 0.10 mm to 0.85 mm. When the given particle size is less than 0.06 mm, the fine powders of the gel particles increase the dust of the product of the superabsorbent polymer. When the given particle size is more than 1.00 mm, the gel particles let a water absorption rate of the product of the superabsorbent polymer become slow. According to one embodiment of the present invention, the particle size distribution of the gel particles is as narrow as possible.

As mentioned above, the dried gel particles have water absorption due to low moisture content (for example, it is not limited that based on a total weight of the gel particles as 100 weight percentages, the moisture content is not more than 5 weight percentages), therefore the gel dried particles are also called preliminary particles of the superabsorbent polymer. For further enhancing the water absorption rate, mechanical strength of gel, an anti-blocking property, a liquid permeability and etc. of the superabsorbent polymer, a process of a surface crosslinking treatment is performed to the particles of the superabsorbent polymer.

Now, many patents disclose methods of the surface crosslinking treatments, for example, the surface crosslinking treatments are performed by distributing the preliminary particles of the superabsorbent polymer and crosslinking agents to organic solvents (Japan Patent Publication No. JP 1981-131608, 1982-44627, 1983-42602 and 1983-117222). The surface crosslinking treatments are performed by using inorganic powders and directly adding crosslinking agents and solution thereof into the superabsorbent polymer (Japan Patent Publication No. JP 1985-163956 and 1985-255814). After adding the crosslinking agents, a steam treatment is then performed (Japan Patent Publication No. JP 1989-113406). The surface treatments are performed by using organic solvents, water and polyhydric alcohol (Japan Patent Publication No. JP 1989-292004 and U.S. Pat. No. 6,346,569). Organic solvents, water, ether and other compounds are used (Japan Patent Publication No. 1990-153903). Although the methods of these surface crosslinking treatments can enhance the water absorption rate and the absorption against pressure, but greatly decrease the centrifuge retention capacity, so that a performance of the practical application of the superabsorbent polymer is reduced. However, the aforementioned drawback does not occur in the surface crosslinking treatments of the present invention.

Referring to FIG. 1 again, after the operation 110, the surface crosslinking reaction is performed to the core layer by using the surface crosslinking agents for forming a first shell layer, in which the first shell layer encapsulates an outer surface of the core layer, as shown in an operation 120. The core layer is the aforementioned preliminary particles of the superabsorbent polymer.

The surface crosslinking agents can comprise, but are not limited to, a polyhydric alcohol, a polyamine, a compound having at least two epoxy groups, an alkylene carbonate and any combination thereof. The specific examples of the aforementioned polyhydric alcohol can comprise, but are not limited to, glycerol, ethylene glycol, diethylene glycol, triethylene glycol, polyethylene glycol, propylene glycol and etc. The specific examples of the aforementioned polyamine can comprise, but are not limited to, ethylenediamine, diethylenediamine or triethylenediamine and etc. The specific examples of the aforementioned compound having at least two epoxy groups can comprise, but are not limited to, sorbitol polyglycidyl ether, polypropylene glycol polyglycidyl ether, ethylene glycol diglycidyl ether, diethylene glycol diglycidyl ether, polyethylene glycol diglycidyl ether, dipropylene glycol polyglycidyl ether and etc.

The specific examples of the aforementioned alkylene carbonate can comprise, but are not limited to, ethylene glycol carbonate, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 1,3-dioxan-2-one, 4,6-dimethyl-1,3-dioxan-2-one, 1,3-dioxepan-2-one and etc. Besides, these surface crosslinking agents can be used alone or in combination.

Based on the amount of the gel made by the free radical polymerization reaction as 100 weight parts, an amount of the surface crosslinking agents is 0.001 weight parts to 10 weight parts, and preferably is 0.005 weight parts to 5 weight parts. When the amount of the surface crosslinking agents is 0.001 weight parts to 10 weight parts, surface crosslinking effect on the superabsorbent polymer is significant, and the absorbent property of the superabsorbent polymer is enhanced to improve performance of the superabsorbent polymer.

According to types of the surface crosslinking agents, methods for adding the surface crosslinking agents can comprise a direct addition or an addition in which a solution of the crosslinking agents is prepared. Solvents for the solution of the crosslinking agents can be water or hydrophilic organic solvent, such as methanol, ethanol, propanol, iso-butanol, acetone, methyl ether, ethyl ether and etc. In some embodiments, the hydrophilic organic solvent preferably is methanol or ethanol as disclosed by U.S. Pat. No. 6,849,665.

Referring to FIG. 1 again, after the operation 120, a surface modification reaction is performed to the first shell layer by using zingiberaceae extracts for forming a second shell layer as shown in an operation 130. In the aforementioned surface modification reaction, hydroxyl groups in chemical structure of the zingiberaceae extracts are used to perform the surface modification reaction for forming a second shell layer on an outer surface of the first shell layer. The surface modification reaction can provide the superabsorbent polymer with antimicrobial and deodorizing abilities, and retain an original absorbent property of the superabsorbent polymer (i.e. a superabsorbent polymer constituted by the core layer and the first shell layer).

The zingiberaceae extracts of the present invention refer to extracts separated from specific parts of zingiberaceae plants by an extraction method, in which phases of the extracts can comprise, but are not limited to, solid, liquid or gas and preferably is solid or liquid in room temperature. The zingiberaceae extracts can be added to the superabsorbent polymer (i.e. a superabsorbent polymer constituted by the core layer and the first shell layer) in the form of a solution. The aforementioned solution refers to a solution formed by the extracts diluted with solvents (hereinafter referred to the solution of the extracts), in which the solvents can comprise organic and inorganic, and the solvents preferably are water. Further, based on the consideration of operability and economic benefits, the zingiberaceae extracts preferably are liquid or diluted aqueous solution.

In some embodiments, the zingiberaceae plants can comprise, but are not limited to, *Curcuma longa*, alpinia zerumbet, *hedychium coronarium*, zingiber zerumbet, alpinia speciose cv variegata, peacock ginger, *Curcuma alismatifolia* and/or *Curcuma roscoeana*. Further, based on the consideration of the antimicrobial and the deodorizing abilities and easy accessibility, the zingiberaceae plants preferably are *hedychium coronarium*.

In some embodiments, the zingiberaceae extracts can comprise, but are not limited to, underground rhizome extracts, stem extracts, flower extracts and/or leaf extracts of zingiberaceae plants, and preferably are the underground rhizome extracts.

In some embodiments, before the zingiberaceae plants are extracted with the solvent, a pulverizing treatment can be performed. The pulverizing treatment can comprise, but is not limited to mechanical crushing methods, such as using crushers, ball mills, hammer crushers and etc. for crushing.

The extraction methods can comprise, but are not limited to, an expression, a solvent extraction, a supercritical fluid extraction, a sub-critical fluid extraction, a direct or indirect distillation, a vacuum distillation and etc. Further, the forementioned extraction methods can be used alone or in combination.

Figure 2:
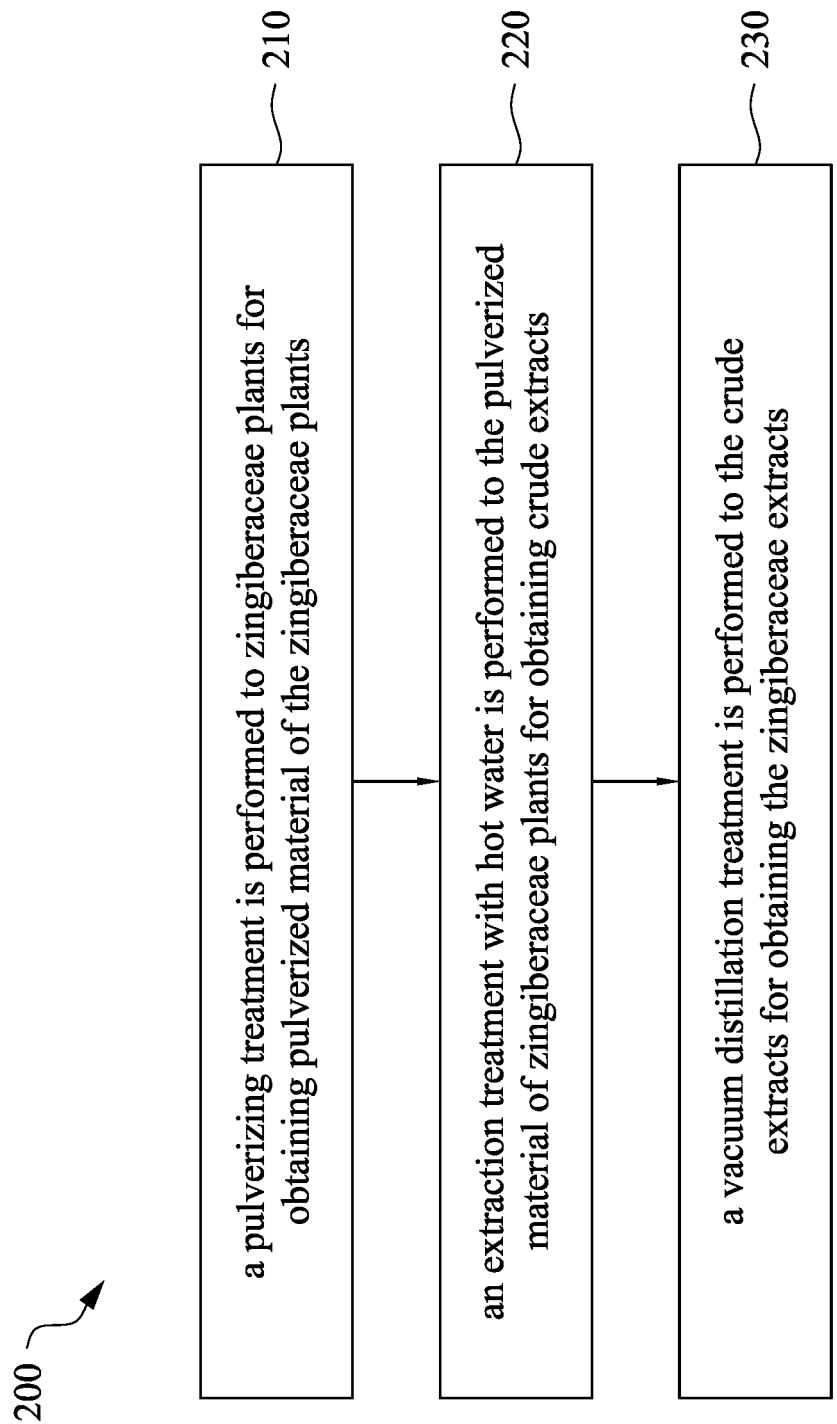
FIG. 2 illustrates a flow chart of an extraction method for extracting zingiberaceae extracts according to an embodiment of the present invention.

In detail, referring to FIG. 2, it illustrates a flow chart of an extraction method for extracting the zingiberaceae extracts according to an embodiment of the present invention. In the extraction method 200 of the zingiberaceae extracts, a pulverizing treatment is performed to the zingiberaceae plants for obtaining pulverized material of the zingiberaceae plants as shown in an operation 210, in which the pulverizing treatment is as mentioned above.

After the operation 210, an extraction treatment with hot water is performed to the pulverized material of the zingiberaceae plants for obtaining crude extracts as shown in an operation 220. Then, a vacuum distillation treatment is performed to the crude extracts for obtaining the zingiberaceae extracts as shown in an operation 230.

For the extraction treatment with hot water, a temperature of the hot water can be 70° C. to 121° C., and preferably is 100° C. Next, a weight ratio of the pulverized material of the zingiberaceae plants and water is 1:1 to 1:10, and preferably is 1:2 to 1:4. Besides, for the vacuum distillation treatment, a pressure is 10 mm Hg to 30 mmHg, and preferably is 20 mmHg. Next, a heating temperature is 40° C. to 60° C., and preferably is 45° C. to 55° C.

In some embodiments, the zingiberaceae extracts can comprise *hedychium coronarium* extracts and a solution of the *hedychium coronarium* extracts. For example, specific examples of the *hedychium coronarium* extracts can be a solution of *hedychium coronarium* extracts produced by Shun Yi Chemical Industry Co., Ltd and First Cosmetics Co., Ltd, essence of the *hedychium coronarium* sold by Yi Cheng Chemical Industry Co., Ltd, Olive Green Handmade Aesthetics Concept Pavilion and Aroma Greens Workshop Co., Ltd., and an aqueous solution of *hedychium coronarium* extracts (item No.: SH-129, and a weight ratio among *hedychium coronarium* extracts, ethanol and water is 8:2:90) produced by Sun Home Chemical Co., Ltd.

For components of the *hedychium coronarium* extracts, components of underground rhizome extracts of the *hedychium coronarium* comprise, but are not limited to, 1,8-cineole, limonene and α-terpineol. Components of stem extracts of the *hedychium coronarium* comprise, but are not limited to, β-ocimene, limonene and 4-carene. Components of leaf extracts of the *hedychium coronarium* comprise, but are not limited to, caryophyllene, limonene, δ-3-carene and β-terpinyl acetate. Components of flower extracts of the *hedychium coronarium* comprise, but are not limited to, (E)-Labda- 8(17), 12-diene-15,16-dial.

There is no special limitation on an amount of the zingiberaceae extracts for the superabsorbent polymer. On the consideration of economic benefits and effect on absorbent ability, based on a weight of the superabsorbent polymer (i.e. a superabsorbent polymer constituted by the core layer and the first shell layer) as 100 weight parts, an amount of the zingiberaceae extracts is 0.005 weight parts to 0.2 weight parts, preferably is 0.005 weight parts to 0.05 weight parts, and more preferably is 0.005 weight parts to 0.02 weight parts. When the amount of the zingiberaceae extracts is less than 0.005 weight parts, antimicrobial property and deodorizing effects of the resulted superabsorbent polymer are poor. When the amount of the zingiberaceae extracts is more than 0.2 weight parts, physical property of the resulted superabsorbent polymer is poor, and absorbent ability of the resulted superabsorbent polymer is decreased. Particularly, when the zingiberaceae extracts are an aqueous solution of the zingiberaceae extracts, if the amount of the zingiberaceae extracts is more than 0.2 weight parts, after the zingiberaceae extracts is added to the particles of the superabsorbent polymer undergone the crosslinking reaction, the zingiberaceae extracts are easy to agglomerate, and can not undergo the following procedures.

In the aforementioned surface modification reaction, the zingiberaceae extracts are first added to the superabsorbent polymer undergone the crosslinking reaction, they are uniformly mixed to coat the zingiberaceae extracts on a surface of the superabsorbent polymer (i.e. an outer surface of the first shell layer). Methods for adding the zingiberaceae extracts can comprise direct addition or addition in form of a solution of the zingiberaceae extracts. In some embodiments, a form of the solution of the zingiberaceae extracts can comprise an aqueous solution or a solution with hydrophilic organic solvents. In some specific examples, the hydrophilic organic solvents can comprise, but are not limited to, methanol, ethanol, propanol, isopropanol, acetone, methyl ether, ethyl ether, and any combination. The hydrophilic organic solvents can preferably be methanol or ethanol.

Mixing devices used in the mixing process can generate a large mixing power for mixing fully and uniformly the superabsorbent polymer and the zingiberaceae extracts. Mixing devices comprise, but are not limited to, a V-type mixer, a column mixer, a high-speed blending mixer, a screw mixer, an airflow mixer, a double-arm kneader, a double-arm conical mixer, a ribbon mixer, a closed system mixer, a pulverizer, a rotary mixer or a screw extruder and etc.

As far as the present invention is concerned, in an application of the zingiberaceae extracts of the present invention is applied to the surface of the superabsorbent polymer undergone the crosslinking reaction and the surface modification reaction is performed to the surface of the superabsorbent polymer, the resulted superabsorbent polymer has antimicrobial and deodorizing abilities and the original absorbent property of the resulted superabsorbent polymer is not decreased. Besides, there are no powders of the superabsorbent polymer leaking into the production equipment, or even suspending in the ambient air of the plant, during the production of the superabsorbent polymer, to harm respiratory tracts of operators. In addition, the procedures for preparing the aforementioned aqueous unsaturated monomers are not particularly limited. The superabsorbent polymer produced by the method of the present invention is suitable for various types of hygienic articles, agricultural and food preservation of the water absorption agents.

On the other hand, for the superabsorbent polymer as an absorbent for diapers, it is necessary to have a certain centrifuge retention capacity (an ability to absorb liquid), and high absorption against pressure, in which the superabsorbent polymer is not damaged by the pressure (for example, the weight of the baby's body) applied from the outside to the absorbent after absorbing the liquid. The damaged superabsorbent polymer loses the ability to absorb the liquid and further the absorbed liquid leaks out of the superabsorbent polymer, thereby increasing rewet of the absorbent. Therefore, the dryness of the diaper is greatly decrease. According to the conclusion of our study, when an index under the absorption against pressure (AAP) of the superabsorbent polymer is not less than 0.8, the rewet of the absorbent of the superabsorbent polymer is greatly decreased. The aforementioned index under the absorption against pressure is calculated according to equation (I) as follows:

$$\text{index under absorption against pressure} = \frac{\text{core shell absorption against pressure } (CS\ AAP)}{\text{absorption against pressure } (AAP)} \quad (I)$$

In some specific examples, the superabsorbent polymer produced by the present invention can be applied to diapers (e.g. Fluffless (using a lot of superabsorbent polymers) or adult diapers) and other sanitary products, so that the diapers have good antimicrobial and deodorizing abilities, and absorbent property of the superabsorbent polymer is not decreased.

In some application examples, the absorbent of the present invention is an absorbent with sheet-like structure which is made by pressing the superabsorbent polymer and hydrophilic fibers. The absorbent is constituted by a non-permeable polyethylene (PE) film as a lower part and the permeable nonwoven fabric as a surface layer, or the superabsorbent polymer is fixed on airlaid and/or a nonwoven fabric. The airlaid is pulverized wood pulp, crosslinked cellulose fibers, and cotton, wool or vinyl acetate fibers.

Based on the weight of the absorbent as 100 weight parts, the content (i.e. core concentration) of the superabsorbent polymer is 20 weight percentages to 100 weight percentages, preferably is 40 weight percentages to 100 weight percentages, and more preferably is 50 weight percentages to 100 weight percentages. The core concentration is a high content of the superabsorbent polymer, such that antimicrobial and deodorizing effects of the present invention can be more effective.

In general, the basic weight of the absorbent of the present invention (a weight per unit area) can be 0.01 g/cm$^2$ to 0.30 g/cm$^2$ and a thickness of the absorbent is not more than 30 mm.

The following embodiments are used to illustrated the applications of the present invention, but they are not used to limit the present invention, it could be made various changes or modifications for a person having ordinary sill in the art without apart from the inspire and scope of the present invention.

Method for producing a solution of *hedychium coronarium* extracts

After *hedychium coronarium* plants were washed, an underground rhizome and a stem thereof were placed in dark to be dried for 1 hour. 250 g of the underground rhizome and the stem were taken, respectively, added with 1500 g of water, and then crushed with a juice machine. Next, the crushed underground rhizome and the crushed stem were heated and refluxed for 4 hours at 100° C. Then, in 20 mm Hg of pressure and at 45° C., a vacuum distillation was performed for obtaining a light-yellow transparent liquid, it was *hedychium coronarium* extracts. 1 g of the *hedychium coronarium* extracts were taken, and added with water to make 100 g of total weight for obtaining a solution of *hedychium coronarium* extracts.

Production of Preliminary Particles of the Superabsorbent Polymer (i.e. a Core Layer) and a First Shell Layer

PREPARATION EXAMPLE 1

583.2 g of water and 540 g of acrylic acid were added to a 2000 mL conical flask and stirred to dissolve, and 437.5 g of 48% sodium hydroxide aqueous solution was dropped to the conical flask, in which a ratio of sodium hydroxide to acrylic acid was 0.85 to 0.95, for a time period of 2 hours and at 15° C. to 40° C. for obtaining sodium acrylate aqueous solution with 42 weight parts, in which 70 mole percentages of acrylic acid were partially neutralized to become sodium acrylate.

Further, 0.9 g of N,N'-methylene bisacrylamide was added to the aforementioned sodium acrylate aqueous solution and temperature thereof was maintained at about 20° C.

Then, 0.3 g of hydrogen peroxide, 3.6 g of sodium bisulfite and 3.6 g of ammonium persulfate as polymerization initiators were added to carry out a free radical polymerization reaction. The gel produced by the reaction was chopped by a cutting mill, and the resulted gel particles with a diameter of not more than 2 mm was screened out according to particle size thereof.

After dried at 130° C. for 2 hours, the gel particles were screened by a mesh with a given particle size of 0.1 mm to 0.85 mm for obtaining dried gel particles (i.e. the preliminary particles of the superabsorbent polymer). Then, the dried gel particles were evaluated by the following evaluation methods and the results were shown in Table 1.

A mixed solution with a volume ration of 1:1:0.5 among ethylene glycol, 1,4-butanediol (produced by Formosa Plastics Co., Ltd.) and methanol was prepared, and 5 g of the aforementioned mixed solution was added to 200 g of the preliminary particles of the superabsorbent polymer, and they were heated at 150° C. for 1 hours, and then cooled for obtaining the superabsorbent polymer of embodiment 1. Then, the superabsorbent polymer was evaluated by the following evaluation methods and the results were shown in Table 1.

PREPARATION EXAMPLES 2 to 3

Preparation examples 2 to 3 were practiced with the same method as in preparation example 1. In preparation example 2, poly(ethylene glycol) diacrylate with molecular weight of 538 mole/g was used as an internal crosslinking agent. In preparation example 3, poly(ethylene glycol) diacrylate with molecular weight of 626 mole/g was used as an internal crosslinking agent, and 2.1 g of aluminum sulfate (27.5% of concentration) was added to perform a reaction at 150° C. for 30 minutes after the method of preparation example 1 for obtaining the superabsorbent polymer of preparation example 3. Specific formulations and evaluated results of preparation examples 2 to 3 were shown in Table 1.

TABLE 1

| | | | preparation example | | |
|---|---|---|---|---|---|
| | | | 1 | 2 | 3 |
| component | monomer | sodium acrylate aqueous solution (weight part) | 42 | 42 | 42 |
| | polymerization initiator | hydrogen peroxide (g) | 0.3 | 0.3 | 0.3 |
| | | sodium bisulfite (g) | 3.6 | 3.6 | 3.6 |
| | | ammonium persulfate (g) | 3.6 | 3.6 | 3.6 |
| | internal crosslinking agent | N,N'-methylene bisacrylamide (g) | 0.9 | 0 | 0 |
| | | poly(ethylene glycol) diacrylate (g) | 0 | 1.3 | 1.1 |
| | surface crosslinking agent | mixed solution of ethylene glycol, 1,4-butanediol and methanol (g) | 5 | 5 | 5 |
| evaluation method | preliminary particles of superabsorbent polymer | centrifuge retention capacity (g/g) | 41.2 | 41.6 | 40.1 |
| | superabsorbent polymer | centrifuge retention capacity (g/g) | 32.7 | 33.7 | 32.5 |
| | | absorption against pressure (g/g) | 22.5 | 24.9 | 25.1 |
| | | core shell absorption against pressure (g/g) | 20.3 | 22.3 | 23.9 |
| | | index of AAP (g/g) | 0.90 | 0.90 | 0.95 |
| | | residual monomer (ppm) | 378 | 433 | 418 |
| | | deodorizing test (level) | 5 | 5 | 5 |
| | | antimicrobial test (level) staphylococcus aureus | 1 | 1 | 1 |
| | | escherichia coli | 1 | 1 | 1 |
| | | odor elimination test (%) | 6 | 5 | 7 |

Production of Second Shell Layer

Embodiment 1

100 g of the superabsorbent polymer of preparation example 1 was taken, and added with 0.5 g of a solution of hedychium coronarium essence (it contained hedychium coronarium essence (produced by Shun Yi Chemical Industry Co., Ltd, and a weight ratio of the hedychium coronarium essence to water was 2.5:100)), in which an amount of the hedychium coronarium extracts was 0.0122 weight parts. Then, they were mixed with a V-shaped mixer for 5 minutes to perform the surface modification reaction for obtaining the superabsorbent polymer of embodiment 1. Then, the superabsorbent polymer was evaluated by the following evaluation methods and the results were shown in Table 2.

Embodiments 2 to 8 and Comparative Embodiments 1 to 5

Embodiments 2 to 8 and comparative embodiments 1 to 5 were practiced with the same method as in embodiment 1 by using various superabsorbent polymers and various surface modification agents. Specific formulations and evaluated results of embodiments 2 to 8 and comparative embodiments 1 to 5 were shown in Tables 2 and 3.

TABLES 2

| | | | \multicolumn{8}{c}{embodiment} |
|---|---|---|---|---|---|---|---|---|---|---|
| | | | 1 | 2 | 3 | 4 | 5 | 6 | 7 | 8 |
| component | superabsorbent polymer (g) | preparation example 1 | 100 | 100 | 100 | 100 | 0 | 0 | 0 | 0 |
| | | preparation example 2 | 0 | 0 | 0 | 0 | 100 | 100 | 0 | 0 |
| | | preparation example 3 | 0 | 0 | 0 | 0 | 0 | 0 | 100 | 100 |
| | surface crosslinking agent (g) | hedychium coronarium essence | 0.5 | 1.0 | 0 | 0 | 0.5 | 0 | 0.5 | 0 |
| | | solution of commercial hedychium coronarium extracts | 0 | 0 | 2 | 0 | 0 | 0 | 0 | 0 |
| | | solution of home-made hedychium coronarium extracts | 0 | 0 | 0 | 2 | 0 | 2 | 0 | 2 |
| evaluation method | surface crosslinked superabsorbent polymer | centrifuge retention capacity (g/g) | 32.3 | 32.1 | 32.4 | 33.1 | 32.8 | 32.9 | 32.6 | 32.1 |
| | | absorption against pressure (g/g) | 22.4 | 21.7 | 20.6 | 22.7 | 24.3 | 24.1 | 24.9 | 24.5 |
| | | core shell absorption against pressure (g/g) | 19.5 | 18.5 | 16.9 | 19.4 | 21.5 | 20.3 | 23.6 | 22.2 |
| | | index of AAP (g/g) | 0.87 | 0.85 | 0.82 | 0.85 | 0.88 | 0.84 | 0.95 | 0.91 |
| | | residual monomer (ppm) | 358 | 364 | 401 | 323 | 442 | 402 | 447 | 459 |
| | | deodorizing test (level) | 1 | 2 | 2 | 3 | 2 | 3 | 2 | 3 |
| | | antimicrobial test (level) staphylococcus aureus | 4 | 4 | 4 | 3 | 4 | 4 | 4 | 3 |
| | | escherichia coli | 4 | 4 | 3 | 4 | 4 | 4 | 4 | 4 |
| | | odor elimination test (%) | 84 | 85 | 76 | 78 | 82 | 79 | 82 | 84 |

Note:
A solution of commercial hedychium coronarium extracts was a solution obtained by mixing hedychium coronarium extracts (produced by Sun Home Chemical Co., Ltd. and item No.:SH-129), ethanol and water (a weight ratio:8:2:90), and then was mixed with water (a weight ratio:1:5). A solution of home-made hedychium coronarium extracts was made by the aforementioned method for producing the solution of hedychium coronarium extracts.

TABLES 3

| | | | \multicolumn{5}{c}{comparative embodiment} |
|---|---|---|---|---|---|---|---|
| | | | 1 | 2 | 3 | 4 | 5 |
| component | superabsorbent polymer (g) | preparation example 1 | 100 | 100 | 100 | 100 | 100 |
| | | preparation example 2 | 0 | 0 | 0 | 0 | 0 |
| | | preparation example 3 | 0 | 0 | 0 | 0 | 0 |
| | surface crosslinking agent (g) | solution of citric acid extracts | 0 | 1.5 | 0 | 0 | 0 |
| | | bamboo powders | 0 | 0 | 1.5 | 0 | 0 |
| | | attapulgite | 0 | 0 | 0 | 3.0 | 0 |
| | | solution of sapindaceae extracts | 0 | 0 | 0 | 0 | 0.5 |
| evaluation method | surface crosslinked superabsorbent polymer | centrifuge retention capacity (g/g) | 32.7 | 31.5 | 32.3 | 32.3 | 32.2 |
| | | absorption against pressure (g/g) | 22.5 | 20.2 | 21.2 | 21.5 | 21.8 |
| | | core hell absorption against pressure (g/g) | 20.3 | 14.5 | 15.2 | 15.0 | 18.5 |
| | | index of AAP (g/g) | 0.90 | 0.72 | 0.72 | 0.70 | 0.85 |
| | | residual monomer (ppm) | 378 | 386 | 337 | 341 | 377 |
| | | deodorizing test (level) | 5 | 4 | 5 | 5 | 1 |
| | | antimicrobial test (level) staphylococcus aureus | 1 | 3 | 1 | 1 | 2 |
| | | escherichia coli | 1 | 3 | 2 | 1 | 4 |
| | | odor elimination test (%) | 6 | 51 | 42 | 33 | 86 |

Note:
A weight ratio of citric acid extracts (produced by Sigma Aldrich Co., Ltd.) to water in a solution of citric acid extracts was 20:100. Bamboo powders were produced by Ban Co., Ltd.. Attapulgite (produced by Long Mao Chemical CO., LTD., particle size was 5 gm) contained aluminium oxide and silicon dioxide, and a weight ratio thereof was 0.12. A solution of sapindaceae extracts was produced by Sun Home Chemical Co., Ltd. and item No. is SH-081.

Preparing of Absorbent

APPLICATION EXAMPLE 1

First, an absorbent-forming machine was used to mix and mold 10.0 g of the superabsorbent polymer of embodiment 1 and 10.0 g of pulverized wood pulp, in which a molding mesh was metal net with 400 mesh (38 μm), and an area of the absorbent was 160 cm² (8 cm×20 cm). Then, the molded absorbent was placed on top of PE film and nonwoven fabric was placed on the molded absorbent. Next, a pressure of 18.39 kPa (area of 160 cm², weight of 30 Kg) was applied to the nonwoven fabric. After the pressure was applied for 5 minutes, the molded absorbent was adhered around with white glue for obtaining the absorbent of application example 1.

APPLICATION EXAMPLES 2 to 5 AND COMPARATIVE APPLICATION EXAMPLES 1 to 4

Application examples 2 to 5 and Comparative application Examples 1 to 4 were practiced with the same method as in application example 1. In application examples 2 to 5 and comparative application examples 1 to 4, the superabsorbent polymers of embodiments 2, 4, 5 and 7, comparative embodiments 1, 2, 3 and 5 were individually correspondingly used. Besides, evaluated results of the superabsorbent polymers of application examples 1 to 5 and comparative application examples 1 to 4 were shown in Table 4.

TABLE 4

|  |  | application example | | | | | comparative application example | | | |
|---|---|---|---|---|---|---|---|---|---|---|
|  |  | 1 | 2 | 3 | 4 | 5 | 1 | 2 | 3 | 4 |
| preparation condition | superabsorbent polymer | embodiment | | | | | comparative embodiment | | | |
|  |  | 1 | 2 | 4 | 5 | 7 | 1 | 2 | 3 | 5 |
|  | basic weight (g/cm$^2$) | 0.08 | 0.07 | 0.08 | 0.08 | 0.08 | 0.07 | 0.06 | 0.07 | 0.08 |
|  | thickness (mm) | 17 | 16 | 17 | 17 | 16 | 17 | 16 | 16 | 17 |
| evaluation method | deodorizing test (level) | 2 | 2 | 2 | 3 | 2 | 5 | 5 | 5 | 2 |
|  | antimicrobial test (level)) staphylococcus aureus | A | 4 | 3 | 4 | 3 | 1 | 2 | 2 |  |
|  | escherichia coli | 4 | 4 | 4 | 3 | 3 | 1 | 2 | 1 | 3 |
|  | rewet amount of the synthetic urine (g) | 1.8 | 2.1 | 2.4 | 2.4 | 1.3 | 3.9 | 8.6 | 8.6 | 2.1 |

Evaluation Methods

In the following evaluation methods, unless otherwise specified, the evaluation methods were performed at room temperature (23±2° C.) and relative air humidity of 45±10%.

1. Absorption Against Pressure (AAP)

Absorption against pressure (AAP) was measured in accordance with the ERT 442.3 (10) test method specified by European Disposables and Nonwovens Association (EDANA). Absorption for a sodium chloride aqueous solution with a concentration of 0.9 weight percentages was measured under a pressure of 4.9 kPa for 60 minutes. The absorption against pressure was preferably not less than 15 g/g and more preferably was 20 g/g to 30 g/g.

2. Core Shell Absorption Against Pressure (CS AAP)

Core shell absorption against pressure (CS AAP) was measured in accordance with the test method of the absorption against pressure, but test time was extended to 240 minutes.

3. Centrifuge Retention Capacity (CRC)

Centrifuge retention capacity was measured in accordance with the ERT 441.3 (10) test method specified by EDANA.

4. Residual Monomer (RAA)

Residual monomer was measured in accordance with the ERT 410.3 (10) test method specified by EDANA.

5. Deodorizing Test of Superabsorbent Polymer

In the deodorizing test, 2.5 g of adult urine was collected in polypropylene bottle with a lid, and the collected urine was subjected on the deodorizing test in 2 hours since urine was excreted. After 2.0 g of the superabsorbent polymer was added to the aforementioned urine, the polypropylene bottle was covered, and the polypropylene bottle was placed at 37° C. for 2 hours. The odor was smelled at a position about 3 cm above the mouth of the bottle, and evaluated according to the following specific criteria for evaluating and ranking, in which deodorizing effect was evaluated by using the average value of the evaluated results from 10 adult urine samples. The specific evaluation criteria were listed below, and the urine odor tested in the conditions without the superabsorbent polymer was used as a standard and ranked as a 5th level.

0: odorless
1: sight odor
2: moderate odor within a tolerable range
3: odor close to the limit of the tolerable range
4: heavy odor slightly more than the limit of the tolerable range
5: strong odor greatly more than the limit of the tolerable range 6. Antimicrobial Test Antimicrobial test was tested in accordance with test methods specified by American Association of Textile Chemists and Colorists (AATCC100). Colony-forming unit of colonies formed on the superabsorbent polymer or the absorbent containing the superabsorbent polymer after they contacted *Staphylococcus aureus* (belonging to gram-positive bacteria) and *Escherichia coli* (belonging to gram-negative bacteria) for 0 hour and 24 hours were measured. The sterilization rate (R %) was used to determine the antimicrobial ability of the superabsorbent polymer or the absorbent against the two strains. The sterilization rate (R %) was calculated according to the following formula (II), and the antimicrobial ability was ranked in 4 levels, and the specific evaluation criteria were shown below:

$$\text{sterilization rate } (R\ \%) = \frac{\text{colony-forming unit (0 hour)} - \text{colony-forming unit (24 hours)}}{\text{colony-forming unit (0 hour)}} \times 100\% \quad \text{(II)}$$

1: no antimicrobial effect in which the sterilization rate was negative or equal to 0%
2: slightly antimicrobial effect in which the sterilization rate was more than 0% to equal to 30%
3: moderate antimicrobial effect in which the sterilization rate was more than 30% to equal to 60%
4: good antimicrobial effect in which the sterilization rate was more than 60%

7. Odor Elimination Test

In odor elimination test (i.e. a test for measuring removal rate of methyl mercaptan), 1.0 g of the superabsorbent polymer to be tested and 25 mL of 0.03% sodium methyl mercaptan aqueous solution were put in a 1 L of airtight container, and stayed at room temperature for 10 minutes. A gas detection tube (produced by GASTEC Co., Ltd., and model: 4L and 4HM) was used to analyze the concentration of the residual gas as the result of the test group. In addition, in the test without using the superabsorbent polymer, the same gas detection tube was used to analyze the concentration of residual gas as the result of the blank group. The removal rate of methyl mercaptan was calculated according to the following formula (III):

$$\text{removal rate (\%)} = \frac{\text{result (blank group)} - \text{result (test group)}}{\text{result (blank group)}} \times 100\% \quad \text{(III)}$$

8. Rewet Test

In rewet (i.e. dryness) test, 4.8 kPa (area of 160 cm$^2$, and a weight of 7.8 Kg) of a weight was placed on the absorbent to be tested, and the weight was applied evenly on the absorbent to be tested. Then, synthetic urine (according to the Jayco synthetic urine described as U.S. Patent Publication No. 20040106745) was added to a center point of the absorbent three times at a frequency of 30 minutes each time, in which a total weight of the synthetic urine was 180 mL. After the synthetic urine was completely added, the weight was put on the absorbent for 30 minutes, and then removed. 30 pieces of filter papers (8 cm×20 cm) in advance measured and recorded as a weight (W1 (g)) were put on the absorbent used to tested, and 4.8 kPa of the weight was immediately put on the filter papers for 5 minutes, so that the aforementioned filter papers absorbed liquid rewet from the absorbent, and the 30 pieces of the filter papers were measured and recorded as a weight (W2 (g)), in which the rewet amount of the synthetic urine rewet from the absorbent was a weight which was calculated by subtracting W2 with W1. The rewet amount was the lower, and dryness of the absorbent was the higher.

9. Deodorizing Test of the Absorbent

Deodorizing test of the absorbent was practiced with the same method as the aforementioned test method of the superabsorbent polymer. In the deodorizing test of the absorbent, 10×10 cm$^2$ of the absorbent was placed in glass dish (inner diameter of 120 mm), and added with 2.5 g of adult urine. Besides, the specific criteria for evaluating and ranking of the deodorizing test for the absorbent were the same as those of the test method for the superabsorbent polymer.

Referring to Tables 2 and 3, according to the results of the odor elimination test, the antimicrobial test and the deodorizing test, in comparison with the superabsorbent polymer produced by comparative embodiment 1 without using surface modification agent, the superabsorbent polymer produced by each embodiment using *hedychium coronarium* extracts or solutions thereof had better antimicrobial property and deodorizing effect. Similarly, in comparison with the superabsorbent polymer produced by comparative embodiment 3 with using the bamboo powders and comparative embodiment 4 with using the attapulgite, the superabsorbent polymer produced by each embodiment using the *hedychium coronarium* extracts or the solutions thereof had better deodorizing and antimicrobial effect. It showed that the *hedychium coronarium* extracts or the solutions thereof were performed surface modification to the superabsorbent polymer for providing the superabsorbent polymer antimicrobial property and an original absorbent property of the superabsorbent polymer were retained.

Next, according to the results of the deodorizing test and the odor elimination test, in comparison with the superabsorbent polymer produced by comparative embodiment 2 with using the citric acid extracts, the superabsorbent polymer produced by each embodiment using *hedychium coronarium* extracts or the solutions thereof had better deodorizing effect. Besides, according to the results of the deodorizing test of the superabsorbent polymer produced by comparative embodiment 1 without using the surface modification agent and comparative embodiment 2 with using the citric acid extracts, the solution of the citric acid extracts can not effectively enhance the deodorizing effect of the superabsorbent polymer.

Additionally, according to the results of the antimicrobial test of *Staphylococcus aureus*, in comparison with the superabsorbent polymer produced by comparative embodiment 5 with using sapindaceae extracts, the superabsorbent polymer produced by each embodiment using *hedychium coronarium* extracts or the solutions thereof had better antimicrobial effect. Besides, according to the results of the antimicrobial test of *Staphylococcus aureus* from the superabsorbent polymer produced by comparative embodiment 1 without using surface modification agent and produced by comparative embodiment 5 with using sapindaceae extracts, the sapindaceae extracts can not effectively enhance the antimicrobial effect of the superabsorbent polymer. Therefore, for these surface modification agents, only *hedychium coronarium* extracts can simultaneously and effectively enhance the deodorizing effect and the antimicrobial effect of the superabsorbent polymer.

Referring to Table 4, according to the results of the deodorizing test and the antimicrobial test, in comparison with the superabsorbent polymer produced by comparative embodiment 1 without using surface modification agent, comparative embodiment 2 with using the citric acid extracts, and comparative embodiment 3 with using the bamboo powders, the superabsorbent polymer produced by each embodiment using *hedychium coronarium* extracts or the solutions thereof had better deodorizing and antimicrobial effect.

Further, according to the results of the rewet amount of the synthetic urine of comparative application example 1 without using surface modification agent and each application examples, *hedychium coronarium* extracts or the solutions thereof can decrease the rewet amount of the synthetic urine of the absorbent, i.e. *hedychium coronarium* extracts or the solutions thereof can enhance long-term absorbent ability. Besides, according to the results of the rewet amount of the synthetic urine of comparative application examples 2 and 3, the citric acid extracts and the bamboo powders decreased long-term absorbent ability of the superabsorbent polymer.

Next, according to the results of the antimicrobial test of *Staphylococcus aureus*, in comparison with the superabsorbent polymer produced by comparative embodiment 5 with using the sapindaceae extracts, the superabsorbent polymer produced by each embodiment using the *hedychium coronarium* extracts or the solutions thereof had better antimicrobial effect. Therefore, for these surface modification agent, only the *hedychium coronarium* extracts can simultaneously and effectively enhance the deodorizing effect, the antimicrobial effect and the long-term absorption ability of the superabsorbent polymer.

In summary, in an application of the superabsorbent polymer and the method for producing the same of the present invention, in where the superabsorbent polymer includes a core layer polymerized with monomers having carboxylic group, a first shell layer formed from a surface crosslinking agent, and a second shell layer formed from tzingiberaceae extracts. By a surface modification on the first shell layer performed from a specific amount of the zingiberaceae extracts, the resulted superabsorbent polymer has a good antimicrobial property and deodorizing effects, and retains an original absorbent property.

Although the present invention has been disclosed in several embodiments as above mentioned, these embodiments do not intend to limit the present invention. Various changes and modifications can be made by those of ordinary skills in the art of the present invention, without departing from the spirit and scope of the present invention. Therefore, the claimed scope of the present invention shall be defined by the appended claims.

What is claimed is:

1. A method for producing superabsorbent polymer, comprising:
    performing a free radical polymerization reaction to monomers having carboxylic group for forming a core layer;
    performing a surface crosslinking reaction to the core layer by using a surface crosslinking agent for forming a first shell layer, wherein the first shell layer encapsulates an outer surface of the core layer; and
    performing a surface modification reaction to the first shell layer by using zingiberaceae extracts for forming a second shell layer, wherein the second shell layer encapsulates an outer surface of the first shell layer;
    wherein based on a total weight of the core layer and the first shell layer as 100 weight parts, an amount of the zingiberaceae extracts is 0.005 weight parts to 0.2 weight parts.

2. The method for producing the superabsorbent polymer of claim 1, wherein the zingiberaceae extracts comprise underground rhizome extracts, stem extracts, flower extracts and/or leaf extracts of zingiberaceae plants.

3. The method for producing the superabsorbent polymer of claim 1, wherein the zingiberaceae extracts are made by an extraction method, wherein the extraction method comprises:
    performing a pulverizing treatment to zingiberaceae plants for obtaining pulverized material of the zingiberaceae plants;
    performing an extraction treatment with hot water to the pulverized material of zingiberaceae plants for obtaining crude extracts; and
    performing a vacuum distillation treatment to the crude extracts for obtaining the zingiberaceae extracts.

4. The method for producing the superabsorbent polymer of claim 2, wherein the zingiberaceae plants comprise *Curcuma longa*, alpinia *zerumbet, hedychium coronarium, zingiber zerumbet*, alpinia speciose cv *variegata*, peacock ginger, *Curcuma alismatifolia* and/or *Curcuma roscoeana*.

* * * * *